_(12)_ United States Patent
Pacheco Villalobos

US011700805B2

(10) Patent No.: US 11,700,805 B2
(45) Date of Patent: Jul. 18, 2023

(54) REGENERATION OF PLANTS IN THE PRESENCE OF HISTONE DEACETYLASE INHIBITORS

(71) Applicant: KWS SAAT SE & CO. KGaA, Einbeck (DE)

(72) Inventor: David Pacheco Villalobos, Einbeck (DE)

(73) Assignee: KWS SAAT SE & CO. KGaA, Einbeck (DE)

( * ) Notice: Subject to any disclaimer, the term of this patent is extended or adjusted under 35 U.S.C. 154(b) by 8 days.

(21) Appl. No.: 16/955,899

(22) PCT Filed: Dec. 21, 2018

(86) PCT No.: PCT/EP2018/086657
§ 371 (c)(1),
(2) Date: Jun. 19, 2020

(87) PCT Pub. No.: WO2019/122360
PCT Pub. Date: Jun. 27, 2019

(65) Prior Publication Data
US 2021/0112740 A1    Apr. 22, 2021

(30) Foreign Application Priority Data
Dec. 22, 2017  (EP) .................................... 17210361

(51) Int. Cl.
*A01H 4/00*    (2006.01)
(52) U.S. Cl.
CPC ............. *A01H 4/008* (2013.01); *A01H 4/005* (2013.01)
(58) Field of Classification Search
CPC ............................ A01H 4/005; C12N 15/8201
See application file for complete search history.

(56) References Cited

U.S. PATENT DOCUMENTS

2016/0212956 A1*  7/2016  Boutilier .................. A01N 37/28

FOREIGN PATENT DOCUMENTS

| CN | 102286522 A | 12/2011 |
| CN | 103461123 A | 12/2013 |
| CN | 104168771 A | 11/2014 |
| CN | 104498505 A | 4/2015 |
| CN | 112105738 A | 12/2020 |
| CN | 112470927 A | 3/2021 |
| JP | 2010220493 A | 10/2010 |
| WO | 94/18313 A1 | 8/1994 |
| WO | 95/09233 A1 | 4/1995 |
| WO | 03/004659 | 1/2003 |
| WO | 03/080809 | 10/2003 |
| WO | 2010/079430 A1 | 7/2010 |
| WO | 2011/072246 | 6/2011 |
| WO | 2011/146121 A1 | 11/2011 |
| WO | 2011/154393 A1 | 12/2011 |
| WO | 2012/001527 | 1/2012 |
| WO | 2012/093833 | 7/2012 |
| WO | 2012/104729 A1 | 8/2012 |
| WO | 2012/138927 A1 | 10/2012 |
| WO | 2012/138939 A1 | 10/2012 |
| WO | 2015/044199 A1 | 4/2015 |
| WO | WO-2015189409 A1 * | 12/2015 | ......... C12N 15/8213 |
| WO | 2016/021973 A1 | 2/2016 |

OTHER PUBLICATIONS

Ye et al (An Efficient Plant Regeneration and Transformation System of Ma Bamboo (Dendrocalamus Iatiflorus Munro) Started from Young Shoot as Explant. Frontiers in Plant Science. 1-12, Jul. 2017). (Year: 2017).*
Char et al (An Agrobacterium-delivered CRISPR/Cas9 system for high-frequency targeted mutagenesis in maize. Plant Biotechnology Journal. 15, pp. 257-268, 2017). (Year: 2017).*
Furuta et al (The CKH2/PKL Chromatin Remodeling Factor Negatively Regulates Cytokinin Responses in *Arabidopsis calli*. Plant Cell Physiol. 52(4): 618-628, 2011). (Year: 2011).*
Kishchenko et al (Production of transgenetic sugarbeet (*Beta vulgaris* L.) plants resistant to phosphinothricin. Cell Biology International 29, 15-19, 2005). (Year: 2005).*
Lee et al (Histone deacetylation-mediated cellular dedifferentiation in *Arabidopsis*. Journal of Plant Physiology 191, 95-100, 2016) (Year: 2016).*
International Search Report and Written Opinion issued in International Application No. PCT/EP2018/086657 dated Feb. 18, 2019.
Kaori Furuta et al: "The CKH2/PKL Chromatin Remodeiing Factor Negativeiy Regulates Cytokinin Responses in *Arabidopsis calli*", Plant and Cell Physiology, vol. 52, No. 4, Feb. 25, 2011 (Feb. 25, 2011), pp. 618-628.
Lee Kyounghee et al: "Histone deacetylation-mediated cellular dedifferentiation in *Arabidopsis*", Journal of Plant Physiology, Elsevier, Amsterdam, NL, vol. 191, Dec. 15, 2015 (Dec. 15, 2015), pp. 95-100.
Kishchenko E M et al: "Transgenic sugar beet tolerant to imidazolinone obtained by-mediated transformation", Cytology and Genetics, Allerton Press, Inc, Heidelberg, vol. 45, No. 3, Jun. 17, 2011 (Jun. 17, 2011), pp. 148-152.
Gurel Ekrem et al; "Biotechnology applications for sugar beet", Critical Reviews In Plant Scien, CRC Press, Boca Raton, FL, US, vol. 27, No. 2, Jan. 1, 2008 (Jan. 1, 2008), pp. 108-140.
Boch et al., "Breaking the code of DNA binding specificity of TAL-type III effectors", Science, 2009, vol. 326, No. 5959, pp. 1509-1512.
Burstein et al., "New CRISPR-Cas systems from uncultivated microbes", Nature, 2017, vol. 542, pp. 237-241.

(Continued)

*Primary Examiner* — Charles Logsdon
*Assistant Examiner* — Wayne Zhong
(74) *Attorney, Agent, or Firm* — Troutman Pepper Hamilton Sanders LLP

(57) ABSTRACT

The present invention relates to the field of plant breeding and in particular to the regeneration of plants from cells and other tissues. More particularly, the invention provides methods and means for improving callus formation and regeneration of plants from callus tissue using a histone deacetylase inhibitor.

11 Claims, 6 Drawing Sheets

(56) References Cited

OTHER PUBLICATIONS

Figure 1:
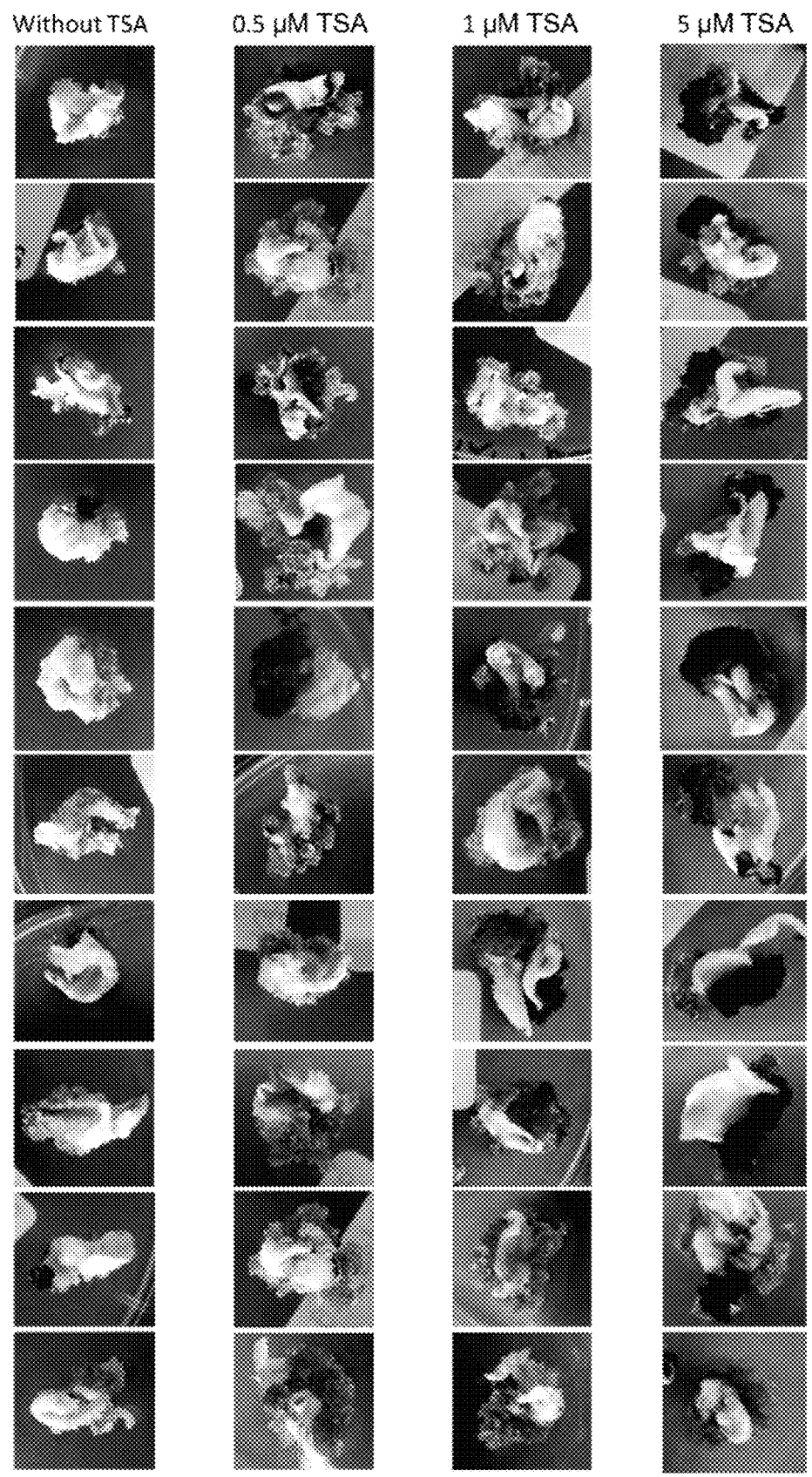

Isalan et al., "A rapid, generally applicable method to engineer zinc fingers illustrated by targeting the HIV-1 promoter", Nature Biotechnology, 2001, vol. 19, No. 7, pp. 656-660.
Ishida et al., "Agrobacterium-mediated transformation of maize", Nature Protocols, 2007, vol. 2, No. 7, pp. 1614-1621.
Ivic-Haymes et al., "Identification of highly regenerative plants within sugar beet (*Beta vulgaris* L.) breeding lines for molecular breeding", In Vitro Cellular and Developmental Biology-Plant, 2005, vol. 41, No. 4, pp. 483-488.
Jinek et al., "A programmable dual-RNA-guided DNA endonuclease in adaptive bacterial immunity", Science, 2012, vol. 337, pp. 816-821.
Kim et al., "Increasing the genome-targeting scope and precision of base editing with engineered Cas9-cytidine deaminase fusions", Nat. Biotechnol., 2017, vol. 35, No. 4, pp. 371-376, doi:10.1038/nbt.3803.
Kishchenko et al., "Production of transgenetic sugarbeet (*Beta vulgaris* L.) plants resistant to phosphinothricin", Cell Biology International, 2005, vol. 29, No. 1, pp. 15-19.
Mishutkina et al., "Sugar beet (*Beta vulgaris* L.) morphogenesis in vitro: effects of phytohormone type and concentration in ths culture medium, type of explants, and plant genotype on shoot regeneration frequency", Russian Journal of Genetics, 2006, vol. 42, No. 2, pp. 150-157.
Moscou et al., "A Simple Cipher Governs DNA Recognition by TAL Effectors", Science, 2009, vol. 326, p. 1501.
Zetsche et al., "Cpf1 Is a Single RNA-Guided Endonuclease of a Class 2 CRISPR-Cas System", Cell, vol. 163, 2015, pp. 759-771.
Liu et al., "Design of polydactyl zinc-finger proteins for unique addressing within complex genomes", Proc. Natl. Acad. Sci. USA, 1997, vol. 94, pp. 5525-5530.
Tomita et al., "Evaluation of the potential for somatic embryogenesis in sugar beet (*Beta vulgaris* L.) breeding lines and improvement of regeneration efficiency", Plant Biotechnology, 2013, vol. 30, No. 5, pp. 479-487.
Zhang, "Creation of green-perpetuating clones based on microspore culture", Full Database of Previous Master Thesis (Electronic Journal) Agricultural Science Series 02, D048-102, published Feb. 15, 2017 (listed in Mar. 11, 2022 Chinese Office Action).
Office Action issued in Chinese Application No. 201880088268 dated Mar. 11, 2022.

\* cited by examiner

A

B

C

REGENERATION OF PLANTS IN THE PRESENCE OF HISTONE DEACETYLASE INHIBITORS

CROSS-REFERENCE TO RELATED APPLICATIONS

This application is a U.S. National Phase of International Patent Application No. PCT/EP2018/086657, filed on Dec. 21, 2018, which claims priority to European Application No. 17210361.6, filed Dec. 22, 2017. The entire contents of these applications are incorporated herein by reference in their entirety.

The present invention relates to the field of plant breeding and in particular to the regeneration of plants from cells and other tissues. More particularly, the invention provides methods and means for improving callus formation and regeneration of plants from callus tissue using a histone deacetylase inhibitor.

Plant regeneration involves the in vitro culture of cells, tissues, and organs under defined physical and chemical conditions. Regeneration has long been known to occur in plants. In plants differentiated cells are able to regenerate into the full array of tissues under appropriate culture conditions. Regeneration can involve direct or indirect organogenesis. In direct regeneration, in vitro organs are directly induced from explant tissues; in indirect regeneration, a de novo organ is typically formed from an intermediate tissue, the callus. Plant calli are undifferentiated structures that can give rise to new tissues. Plant leaves, shoots, roots, and embryos can variously be elicited from a growing callus by treating it with different ratios of hormones.

Generally, three phases can be recognized throughout plant regeneration. First, somatic cells of explant tissues can respond to hormonal signals to acquire features similar to meristematic cells, a process known as "dedifferentiation". Second, callus cells with organogenic competence are reprogrammed and determined for specific organ formation under the influence of hormone balance. The third regeneration phase, morphogenesis, is independent of exogenously supplied hormones. Thus, exogenous hormone treatment is the critical factor triggering early developmental events in in vitro regeneration.

However, obtaining dedifferentiated cells (callus) that can regenerate into whole plants is not always feasible for many plant species. Sugar beet is known to be recalcitrant for dedifferentiation and plant regeneration. These difficulties were major obstacles for obtaining transgenic sugar beets for example through an *Agrobacterium*-mediated transformation procedure. Since decades breeders and researchers are working on the development of more efficient protocols for transformation and regeneration of plants recalcitrant to callus formation. Typically, such plants show genotypic variations causing drastic differences of rates of callus and shoot formation between different lines (Ivic-Haymes & Smigocki (2005), "Identification of highly regenerative plants within sugar beet (*Beta vulgaris* L.) breeding lines for molecular breeding." *In Vitro Cellular and Developmental Biology-Plant*, 41(4), 483-488; Mishutkina & Gaponenko (2006), "Sugar beet (*Beta vulgaris* L.) morphogenesis in vitro: effects of phytohormone type and concentration in the culture medium, type of explants, and plant genotype on shoot regeneration frequency." *Russian Journal of Genetics*, 42(2), 150-157; Tomita et al. (2013), "Evaluation of the potential for somatic embryogenesis in sugar beet (*Beta vulgaris* L.) breeding lines and improvement of regeneration efficiency." *Plant Biotechnology*, 30(5), 479-487.). Often regeneration for certain genotypes is not feasible at all. Kishchenko et al. 2005 ("Production of transgenetic sugar-beet (*Beta vulgaris* L.) plants resistant to phosphinothricin." *Cell biology international*, 29(1), 15-19.) and Kagami at el. 2015 ("Sugar beet (*Beta vulgaris* L.)." *Agrobacterium Protocols: Volume* 1, 335-347.) disclose well-known protocols for the transformation of sugar beet, however these protocols show strong genotype dependency.

In context of the induction of haploid embryogenesis in order to produce double haploid plant from e.g. microspores, it has been found that by adding HDACi (histone deacetylases inhibitors) like trichostatin A (TSA) to the culture medium a large increase in the proportion of cells derived from male gametophytes of diverse plant species undergoes embryogenic growth (WO 2015/044199 A1). However, the use of TSA in formation of callus and regeneration was rather sobering. In Furuta et al. ((2011), "The CKH2/PKL chromatin remodeling factor negatively regulates cytokinin responses in *Arabidopsis calli*." *Plant and cell physiology*, 52(4), 618-628.) the characterization of the mutant cytokinin-hypersensitive 2 (ckh2) in *Arabidopsis* showed that histone deacetylation is intimately related to cytokin-induced callus growth. TSA application has been used as partial substitute for cytokinins in the promotion of callus growth from hypocotyl explants. Cytokinin (Kinetin) and TSA did not induce callus growth neither alone nor in combination. Recently, Lee et al. ((2016), "Histone deacetylation-mediated cellular dedifferentiation in *Arabidopsis*." *Journal of plant physiology*, 191, 95-100.) described that histone deacetylation is required for callus formation from leaf explants in *Arabidopsis*. However, treatment with TSA led to defective callus formation. In support of this, a subset of HDAC genes was up-regulated in calli and some hdac mutants showed reduced capability of callus formation.

Summarizing these findings, it seems that in *Arabidopsis* TSA has an opposite effect on callus induction from leaves and, in combination with cytokinin, TSA does not induce callus in hypocotyl explants.

Surprisingly, the inventors found that histone deacetylase inhibitors (HDACi) like TSA have a positive effect on callus initiation in plants of the species *Beta vulgaris* like sugar beet. Such effect of TSA and other HDACis has not been proved for indirect regeneration protocols or to overcome recalcitrance in e.g. sugar beet genotypes before. Importantly, neither TSA nor any other HDACi has been used in any transformation protocol of crop, aiming to improve the efficiency.

Thus, a first aspect of the present invention is the use of a HDACi in a method for inducing callus formation or producing callus having an enhanced capability of shoot regeneration from plant cells, in particular from somatic or embryonic plant cells and preferably from an explant or a part thereof isolated from a plant. Embryonic plant cells are preferably non-haploid cells. Enhanced capability of shoot regeneration is assessed in comparison with the same method for producing callus and the same genotype but without the use of the HDACi.

The present invention provides a method for inducing callus formation or producing callus having an enhanced capability of shoot regeneration from at least one plant cell, comprising the step of cultivating the at least one plant cell in the presence of a HDACi. In principle, it is sufficient to use only one plant cell to carry out the method according to the present invention. Thus, if the plural "plant cells" is used in the following the wording must not be understood in that a minimum number of plant cells would be required.

Plant cells suitable for use in the method of the present invention include embryonic plant cells and somatic plant cells. The way how these plant cells are provided is not important for the method according to the present invention. For example, embryonic or somatic plant cells can be provided from an explant isolated from a plant. Which part of a plant is eligible for obtaining an explant depends on the particular plant species. Generally, suitable plant cells can be obtained for instances from hypocotyl, petiole, shoot and axial meristems, leaf blade, flower, parenchyma or parenchymatic cells, internode, seeds, embryos and roots of a plant.

In terms of the invention, "histone deacetylases inhibitor" or "HDACi" refers to any chemical compound that inhibits histone deacetylase. It is understood, that the HADCi can be a single compound or a combination of several compounds. A preferred class of compounds suitable to provide the desired histone deacetylase inhibitory activity is hydroxamic acids and hydroxamates, such as trichostatin A (TSA), vorinostat (SAHA), belinostat (PXD101), LAQ824, and panobinostat (LBH589). According to the invention, it is preferred to use TSA as the histone deacetylase inhibitor. Other examples of HDACis for use according to the invention include cyclic tetrapeptides (such as trapoxin B) and depsipeptides, benzamides such as entinostat (MS-275), CI994, and mocetinostat (MGCD0103), electrophilic ketones and aliphatic acid compounds such as phenylbutyrate and valproic acid.

Cultivating plant cells may comprise growing the plant cells in a medium comprising a HDACi. Alternatively or additionally, the HDACi can be introduced into the plant cells, for example via bombardment, electroporation or microinjection or any other method known to the skilled person. According to the invention it is preferred to grow the plant cells in a HDACi-containing medium. The cultivating step can be carried out using any callus-inducing medium (CIM) well-known in the art. In principle, several types of basal salt mixtures can be used for cell culture, but most preferred, the medium comprises modified Murashige and Skoog medium, White's medium, or woody plant medium.

According to a preferred aspect of the invention, the CIM is supplemented with the HDACi. The concentration of HDACi in the medium can range from about 0.01 µM up to about 5.0 µM. It was found that different plants tolerate HDACi differently. At least in some plants, concentrations of HDACi, in particular TSA exceeding 5.0 µM may be cytotoxic. In order to achieve the desired boost of callus formation, the concentration of HDACi in the medium is preferably in a range of 0.01 µM to 1.0 µM.

In addition to the HDACi, one or more further additives can be used in the culture medium. For example, the culture medium can be supplemented with plant growth regulators, such as auxins, cytokinins, and gibberellins, to initiate callus formation. Vitamins can be provided to enhance growth, such as Gamborg B5 vitamins. Enrichment with nitrogen, phosphorus and potassium also proved to be helpful.

Surprisingly, it was found that the method of the invention is suitable for inducing callus formation or producing callus having an enhanced capability of shoot regeneration even in recalcitrant plant species or plant genotypes. Thus, using the method of the invention it is possible to improve indirect regeneration in recalcitrant plant species or plant genotypes.

In a preferred embodiment of the present invention the induction of callus formation can be followed by the regeneration of shoots from the callus tissue. As the use of HDACi, in particular TSA, according to the present invention promotes callus formation the result is an improved method for regenerating plants. The inventors found that frequently more callus has formed by use of HDACi, in particular TSA, but even if not more or even less callus tissue has been formed the quality of the callus was clearly improved, i.e. the formed callus shows an enhanced capability of shoot regeneration. Thus, the present invention provides a method for regenerating shoots from a callus tissue, comprising the step of
 (a) Inducing callus formation from at least one plant cell as described above and
 (b) cultivating the callus tissue obtained in step (a) under conditions promoting the growing of shoots out of the callus tissue.

Suitable cultivation conditions are well-known to the skilled person. Depending on the plant in question, these conditions may vary.

According to another aspect of the invention, the beneficial effect of HDACi on callus formation can be exploited in methods of transformation of plant cells as well as in methods wherein the genome of a plant cell is modified. It was found, that in recalcitrant plant species or plant genotypes, transformation efficiency can be improved by using HDACi. Thus, the invention also concerns the use of a HDACi in a method of transformation of a plant cell and the use of a HDACi in a method of modifying the genome of a plant cell.

Accordingly, the invention provides a method for transforming a plant cell, comprising the following steps:
 (a) inducing callus formation from at least one plant cell as described above, and
 (b) introducing into a plant cell to be used in step (a) and/or into a cell of the callus obtained in step (a) at least one nucleotide sequence of interest.

Step (a) of inducing callus formation is performed using the method described herein above. Preferably, callus formation is induced in the presence of a TSA which can be added to the medium or directly introduced into the plant cells.

In step (b), a cell is transformed by introducing a nucleic acid molecule into the cell in a manner to cause stable or transient expression of the nucleic acid sequence. Transformation of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium*-mediated transformation.

According to one embodiment of the present invention, the at least one nucleotide sequence of interest is introduced into the plant cell to be used in step (a) of inducing callus formation. It is understood that in this case step (b) is carried out before step (a). According to another embodiment of the invention the at least one nucleotide sequence of interest is introduced into a cell of the callus obtained in step (a). It is understood that in this case, step (b) is carried out after step (a). According to a further embodiment of the invention the at least one nucleotide sequence of interest is introduced into a plant cell during callus induction/formation, i.e. step (a) and (b) are carried out in parallel or simultaneously. Additionally, it is possible to introduce nucleotide sequences of interest both into the cell to be used for callus formation and into the cell of the callus resulting from step (a). According to this embodiment the method includes the following steps:
- (i) introducing into a plant cell at least one nucleotide sequence of interest,
- (ii) inducing callus formation from the cell obtained in step (i) and
- (iii) introducing at least one nucleotide sequence of interest into a cell of the callus obtained in step (ii).

The step of introducing the at least one nucleotide sequence of interest can be performed using any suitable method commonly known in the art. A number of methods is available to transfer nucleic acids of interest into plant cells. An exemplary vector mediated method is *Agrobacterium*-mediated transformation, as described, for example, by Lindsay & Gallois, 1990, Journal of Experimental Botany, and Kischenko et al., 2005, Cell Biology International for sugar beet, by Ishida et al., 2007, ("*Agrobacterium*-mediated transformation of maize." *Nature protocols*, 2(7), 1614-1621) for corn, or by the PureWheat Technology from Japan Tobacco company for wheat. Other suitable techniques include particle bombardment, vacuum infiltration, floral dipping, and electroporation.

The nucleotide sequence of interest according to the invention may be a DNA or RNA sequence, e.g. mRNA, siRNA, miRNA etc. More particularly, the nucleotide sequence of interest encodes at least one phenotypic trait. Preferably, the phenotypic trait conferred by the DNA or RNA can be selected from the group consisting of resistance/tolerance to biotic stress, including pathogen resistance/tolerance, wherein the pathogen can be a virus, bacterial, fungal or animal pathogen, resistance/tolerance to abiotic stress including chilling resistance/tolerance, drought stress resistance/tolerance, osmotic resistance/tolerance, heat stress resistance/tolerance, cold or frost stress resistance/tolerance, oxidative stress resistance/tolerance, heavy metal stress resistance/tolerance, salt stress or water logging resistance/tolerance, lodging resistance/tolerance, shattering resistance/tolerance, or resistance/tolerance against one or more herbicides like glyphosate, glufosinate, 2,4-D, Dicamba, ALS inhibitors et cetera. The at least one phenotypic trait of interest can also be selected from the group consisting of the modification of a further agronomic trait of interest including yield increase, flowering time modification, seed color modification, endosperm composition modification, nutritional content modification or metabolic engineering of a pathway of interest.

A nucleic acid (molecule) or nucleotide (sequence) or polynucleotide, as used herein, refers to both DNA and RNA. DNA also includes cDNA and genomic DNA. A nucleic acid molecule can be single- or double-stranded, and can be synthesized chemically or produced by biological expression in vitro or even in vivo.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

Further, the invention also provides a method for modifying the genome of a plant cell, comprising the following steps
- (a) inducing callus formation from at least one plant cell as described above, and
- (b) modifying the genome of a plant cell to be used in step (a) and/or of a cell of the callus tissue obtained in step (a) by introducing into said cell a site specific effector enzyme which preferably recognizes a predetermined site in the genome of said cell, and optionally a repair nucleic acid molecule,
  wherein the modification of said genome is selected from
  - i. a replacement of at least one nucleotide;
  - ii. a deletion of at least one nucleotide;
  - iii. an insertion of at least one nucleotide; or
  - iv. any combination of i.-iii.

Step (a) of inducing callus formation is performed by the method described herein above. Preferably, callus formation is induced in the presence of TSA as the HDACi; which can be added to the medium or introduced directly into the plant cells.

In step (b), modifying the genome of the cell is accomplished by means of a double-stranded DNA break (DSB) inducing enzyme or a single stranded DNA break (DSB) inducing enzyme (nickase) which preferably recognizes a predetermined site in the genome of said cell.

The step of modifying the genome can be carried out before and/or after induction of callus formation. Thus, according to a first aspect of the invention, the genome of a plant cell is modified as described in step (b) and the resulting modified plant cell is then used in a subsequent step (a) of inducing callus formation. According to another aspect of the invention, step (a) of inducing callus formation is carried out first and subsequently at least one cell of the resulting callus tissue is modified in step (b) by means of a site specific effector enzyme. According to a further embodiment of the invention the genome of a plant cell is modified as described in step (b) during callus induction/formation, i.e. step (a) and (b) are carried out in parallel or simultaneously. Furthermore, it is possible to modify the genome of both the plant cell to be used in the step of callus formation and a cell of the callus tissue resulting from the step of inducing callus formation. According to this aspect of the invention, the method includes the steps of
- (i) modifying the genome of a plant cell,
- (ii) inducing callus formation from the cell resulting from step (i) and
- (iii) modifying the genome of a cell of the callus tissue obtained in step (ii).

Examples of site specific effector enzymes are, in particular, enzymes such as nucleases, nickases, recombinases, transposases, base editors or molecular complexes including these tools. These effectors have the capacity to introduce a double-strand cleavage (double-stranded DNA break inducing enzyme (DSBI)) or single-strand cleavage (single-stranded DNA break inducing enzyme (SSBI)) into a genomic target site, or have the capacity to introduce a targeted modification, including a point mutation, an insertion, or a deletion, into a genomic target site of interest. A site-specific effector enzyme can act on its own, or in combination with other molecules as part of a molecular complex. The site-specific effector enzyme can be present as fusion molecule, or as individual molecules associating by or being associated by at least one of a covalent or non-covalent interaction so that the components of the site-specific effector complex are brought into close physical proximity. The complex may include a repair template to make a targeted sequence conversion or replacement at the target site. A repair template (RT) represents a single-stranded or double-stranded nucleic acid sequence, which can be provided during any genome editing causing a double-strand or single-strand DNA break to assist the targeted repair of said DNA break by providing a RT as template of known sequence assisting homology-directed repair.

As used herein, a "double-stranded DNA break inducing enzyme" or "DSBI enzyme" is an enzyme capable of inducing a double-stranded DNA break at a particular nucleotide sequence, called the "recognition site". The double-stranded DNA break (DSB)-inducing enzyme can, for example, be selected from the group consisting of meganuclease, TAL effector nuclease, zinc finger nuclease, CRISPR systems like CRISPR/Cas9, CRISPR/Cpf1, CRISPR/Csm1, CRISPR/MAD7, CRISPR/CasX or CRISPR/CasY. Rare-cleaving endonucleases are DSBI enzymes that have a recognition site of preferably about 14 to 70 consecutive nucleotides, and therefore have a very low frequency of cleaving, even in larger genomes such as most plant genomes. Homing endonucleases, also called meganucleases, constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrast to the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level. A list of other rare cleaving meganucleases and their respective recognition sites is provided in Table I of WO 03/004659 (pages 17 to 20) (incorporated herein by reference).

Furthermore, methods are available to design custom-tailored rare-cleaving endonucleases that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO 94/18313 or WO 95/09233 and in Isalan et al., 2001, Nature Biotechnology 19, 656-660; Liu et al. 1997, Proc. Natl. Acad. Sci. USA 94, 5525-5530).

Another example of custom-designed endonucleases include the so-called TALE nucleases (TALENs), which are based on transcription activator-like effectors (TALEs) from the bacterial genus *Xanthomonas* fused to the catalytic domain of a nuclease (e.g. FokI or a variant thereof). The DNA binding specificity of these TALEs is defined by repeat-variable diresidues (RVDs) of tandem-arranged 34/35-amino acid repeat units, such that one RVD specifically recognizes one nucleotide in the target DNA. The repeat units can be assembled to recognize basically any target sequences and fused to a catalytic domain of a nuclease create sequence specific endonucleases (see e.g. Boch et al., 2009, Science 326:p 1509-1512; Moscou and Bogdanove, 2009, Science 326:p 1501; and WO 2010/079430, WO 2011/072246, WO 2011/154393, WO 2011/146121, WO 2012/001527, WO 2012/093833, WO 2012/104729, WO 2012/138927, WO 2012/138939). WO2012/138927 further describes monomeric (compact) TALENs and TALENs with various catalytic domains and combinations thereof.

Recently, a new type of customizable endonuclease system has been described; the so-called CRISPR/Cas system. A CRISPR system in its natural environment describes a molecular complex comprising at least one small and individual non-coding RNA in combination with a Cas nuclease or another CRISPR nuclease like a Cpf1 nuclease (Zetsche et al., "Cpf1 Is a Single RNA-Guides Endonuclease of a Class 2 CRISPR-Cas System", Cell, 163, pp. 1-13, October 2015) which can produce a specific DNA double-stranded break. Presently, CRISPR systems are categorized into 2 classes comprising five types of CRISPR systems, the type II system, for instance, using Cas9 as effector and the type V system using Cpf1 as effector molecule (Makarova et al., Nature Rev. Microbiol., 2015). In artificial CRISPR systems, a synthetic non-coding RNA and a CRISPR nuclease and/or optionally a modified CRISPR nuclease, modified to act as nickase or lacking any nuclease function, can be used in combination with at least one synthetic or artificial guide RNA or gRNA combining the function of a crRNA and/or a tracrRNA (Makarova et al., 2015, supra). The immune response mediated by CRISPR/Cas in natural systems requires CRISPR-RNA (crRNA), wherein the maturation of this guiding RNA, which controls the specific activation of the CRISPR nuclease, varies significantly between the various CRISPR systems which have been characterized so far. Firstly, the invading DNA, also known as a spacer, is integrated between two adjacent repeat regions at the proximal end of the CRISPR locus. Type II CRISPR systems code for a Cas9 nuclease as key enzyme for the interference step, which system contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region. Recombinant gRNA molecules can comprise both the variable DNA recognition region and also the Cas interaction region and thus can be specifically designed, independently of the specific target nucleic acid and the desired Cas nuclease. As a further safety mechanism, PAMs (protospacer adjacent motifs) must be present in the target nucleic acid region; these are DNA sequences which follow on directly from the Cas9/RNA complex-recognized DNA. The PAM sequence for the Cas9 from *Streptococcus pyogenes* has been described to be "NGG" or "NAG" (Standard IUPAC nucleotide code) (Jinek et al, "A programmable dual-RNA-guided DNA endonuclease in adaptive bacterial immunity", Science 2012, 337: 816-821). The PAM sequence for Cas9 from *Staphylococcus aureus* is "NNGRRT" or "NNGRR(N)". Further variant CRISPR/Cas9 systems are known. Thus, a *Neisseria meningitidis* Cas9 cleaves at the PAM sequence NNNNGATT. A *Streptococcus thermophilus* Cas9 cleaves at the PAM sequence NNAGAAW. Recently, a further PAM motif NNNNRYAC has been described for a CRISPR system of *Campylobacter* (WO 2016/021973 A1). For Cpf1 nucleases it has been described that the Cpf1-crRNA complex, without a tracrRNA, efficiently recognize and cleave target DNA proceeded by a short T-rich PAM in contrast to the commonly G-rich PAMs recognized by Cas9 systems (Zetsche et al., supra). Furthermore, by using modified CRISPR polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized. Further CRISPR effectors like CasX and CasY effectors originally described for bacteria, are meanwhile available and represent further effectors, which can be used for genome engineering purposes (Burstein et al., "New CRISPR-Cas systems from uncultivated microbes", Nature, 2017, 542, 237-241).

Furthermore, modified Cas or Cpf1 variants or any other modified CRISPR effector variants, e.g., Cas9 variants, can be used according to the methods of the present invention as part of a base editing complex, e.g. BE3, VQR-BE3, EQR-BE3, VRER-BE3, SaBE3, SaKKH-BE3 (see Kim et al., Nat. Biotech., 2017, doi:10.1038/nbt.3803). Therefore, according to the present invention, artificially modified CRISPR nucleases are envisaged, which might indeed not be any "nucleases" in the sense of double-strand cleaving enzymes, but which are nickases or nuclease-dead variants, which still have inherent DNA recognition and thus binding ability.

A "base editor" as used herein refers to a protein or a fragment thereof having the same catalytical activity as the protein it is derived from, which protein or fragment thereof, alone or when provided as molecular complex, referred to as base editing complex herein, has the capacity to mediate a targeted base modification, i.e., the conversion of a base of interest resulting in a point mutation of interest. Preferably, the at least one base editor in the context of the present invention is temporarily or permanently linked to at least one site-specific effector, or optionally to a component of at least one site-specific effector complex. The linkage can be covalent and/or non-covalent.

The cleavage site of a DSBI enzyme or a SSBI enzyme relates to the exact location on the DNA where the double-stranded DNA break is induced. The cleavage site may or may not be comprised in (overlap with) the recognition site of the DSBI or SSBI enzyme and hence it is said that the cleavage site of a DSBI or SSBI enzyme is located at or near its recognition site. The recognition site of a DSBI or SSBI enzyme, also sometimes referred to as binding site, is the nucleotide sequence that is (specifically) recognized by the DSBI or SSBI enzyme and determines its binding specificity. For example, a TALEN or ZNF monomer has a recognition site that is determined by their RVD repeats or ZF repeats respectively, whereas its cleavage site is determined by its nuclease domain (e.g. FokI) and is usually located outside the recognition site. In case of dimeric TALENs or ZFNs, the cleavage site is located between the two recognition/binding sites of the respective monomers, this intervening DNA region where cleavage occurs being referred to as the spacer region.

A person skilled in the art would be able to either choose a DSBI or SSBI enzyme recognizing a certain recognition site and inducing a DSB or SSB at a cleavage site at or in the vicinity of the preselected site or engineer such a DSBI or SSBI enzyme. Alternatively, a DSBI or SSBI enzyme recognition site may be introduced into the target genome using any conventional transformation method or by crossing with an organism having a DSBI or SSBI enzyme recognition site in its genome, and any desired DNA may afterwards be introduced at or in the vicinity of the cleavage site of that DSBI or SSBI enzyme.

In a particularly preferred aspect of this embodiment, a repair nucleic acid molecule is additionally introduced into the plant cell.

As used herein, a "repair nucleic acid molecule" is a single-stranded or double-stranded DNA molecule or RNA molecule that is used as a template for modification of the genomic DNA at the preselected site in the vicinity of or at the cleavage site. As used herein, "use as a template for modification of the genomic DNA", means that the repair nucleic acid molecule is copied or integrated at the preselected site by homologous recombination between the flanking region(s) and the corresponding homology region(s) in the target genome flanking the preselected site, optionally in combination with non-homologous end-joining (NHEJ) at one of the two end of the repair nucleic acid molecule (e.g. in case there is only one flanking region). Integration by homologous recombination will allow precise joining of the repair nucleic acid molecule to the target genome up to the nucleotide level, while NHEJ may result in small insertions/deletions at the junction between the repair nucleic acid molecule and genomic DNA.

As used herein, "a modification of the genome", means that the genome has changed by at least one nucleotide. This can occur by replacement of at least one nucleotide and/or a deletion of at least one nucleotide and/or an insertion of at least one nucleotide, as long as it results in a total change of at least one nucleotide compared to the nucleotide sequence of the preselected genomic target site before modification, thereby allowing the identification of the modification, e.g., by techniques such as sequencing or PCR analysis and the like, of which the skilled person will be well aware.

As used herein "a preselected site" or "predefined site" indicates a particular nucleotide sequence in the genome (e.g. the nuclear genome) at which location it is desired to insert, replace and/or delete one or more nucleotides. This can e.g. be an endogenous locus or a particular nucleotide sequence in or linked to a previously introduced foreign DNA or transgene. The preselected site can be a particular nucleotide position at (after) which it is intended to make an insertion of one or more nucleotides. The preselected site can also comprise a sequence of one or more nucleotides which are to be exchanged (replaced) or deleted.

As used in the context of the present application, the term "about" means+/−10% of the recited value, preferably +/−5% of the recited value. For example, about 100 nucleotides (nt) shall be understood as a value between 90 and 110 nt, preferably between 95 and 105.

As used herein, a "flanking region", is a region of the repair nucleic acid molecule having a nucleotide sequence which is homologous to the nucleotide sequence of the DNA region flanking (i.e. upstream or downstream) of the preselected site. It will be clear that the length and percentage sequence identity of the flanking regions should be chosen such as to enable homologous recombination between said flanking regions and their corresponding DNA region upstream or downstream of the preselected site. The DNA region or regions flanking the preselected site having homology to the flanking DNA region or regions of the repair nucleic acid molecule are also referred to as the homology region or regions in the genomic DNA.

To have sufficient homology for recombination, the flanking DNA regions of the repair nucleic acid molecule may vary in length, and should be at least about 10 nt, about 15 nt or about 20 nt in length. However, the flanking region may be as long as is practically possible (e.g. up to about 100-150 kb such as complete bacterial artificial chromosomes (BACs). Preferably, the flanking region will be about 50 nt to about 2000 nt, e.g. about 100 nt, 200 nt, 500 nt or 1000 nt. Moreover, the regions flanking the DNA of interest need not be identical to the homology regions (the DNA regions flanking the preselected site) and may have between about 80% to about 100% sequence identity, preferably about 95% to about 100% sequence identity with the DNA regions flanking the preselected site. The longer the flanking region, the less stringent the requirement for homology. Furthermore, to achieve exchange of the target DNA sequence at the preselected site without changing the DNA sequence of the adjacent DNA sequences, the flanking DNA sequences should preferably be identical to the upstream and downstream DNA regions flanking the preselected site.

As used herein, "upstream" indicates a location on a nucleic acid molecule which is nearer to the 5' end of said nucleic acid molecule. Likewise, the term "downstream" refers to a location on a nucleic acid molecule which is nearer to the 3' end of said nucleic acid molecule. For avoidance of doubt, nucleic acid molecules and their sequences are typically represented in their 5' to 3' direction (left to right).

In order to target sequence modification at the preselected site, the flanking regions must be chosen so that 3' end of the upstream flanking region and/or the 5' end of the downstream flanking region align(s) with the ends of the predefined site. As such, the 3' end of the upstream flanking region determines the 5' end of the predefined site, while the 5' end of the downstream flanking region determines the 3' end of the predefined site.

As used herein, said preselected site being located outside or away from said cleavage (and/or recognition) site, means that the site at which it is intended to make the genomic modification (the preselected site) does not comprise the cleavage site and/or recognition site of the DSBI or SSBI enzyme, i.e. the preselected site does not overlap with the cleavage (and/or recognition) site. Outside/away from in this respect thus means upstream or downstream of the cleavage (and/or recognition) site.

The modified plant cell that has been transformed or gene edited according to the methods of the present invention and possibly has a modified genome can be regenerated into a whole (fertile) plant. Thus, in a preferred aspect of the invention, the transformation of a plant cell or the modification of a genome of a plant cell, respectively, is followed by a step of regenerating a plant.

Accordingly, the present invention provides a method for producing a transgenic plant comprising the following steps:
  (a) transforming a plant cell according to the method described above, and
  (b) regenerating a transgenic plant from the transgenic cell resulting from step (a) or from a transgenic cell derived therefrom.

Transgenic plants or transgenic cells of step (b) comprise the at least one nucleotide sequence of interest introduced in step (a) as transgene, either stably or transiently.

Further, the present invention also provides a method of producing a genetically modified plant comprising the following steps
  (a) modifying the genome of a plant cell according to the method described above, and
  (b) regenerating a plant from the cell resulting from step (a) or of from a cell (comprising the modification of the genome generated in step (a)) derived therefrom.

Regeneration techniques rely on manipulation of certain phytohormones in a tissue culture growth medium, occasionally relying on a biocide and/or herbicide marker that can been introduced together with the desired nucleotide sequence(s) of interest. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, protoplasts, immature or mature embryos, embryonic tissue, meristematic tissues, organs, or parts thereof. Such regeneration techniques are described generally in Klee (1987) Ann. Rev. of Plant Phys. 38:467486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

The present invention is applicable to any plant species, whether monocot or dicot. Preferably, plants which may be subject to the methods and uses of the present invention are plants which do not belong to the genus of *Arabidopsis* or which are not plants of the species *Arabidopsis thaliana*. More preferably, plants which may be subject to the methods and uses of the present invention are selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia fournieri, Allium cepa, Allium fistulosum, Allium sativum, Helianthus annuus, Helianthus tuberosus* and/or *Allium tuberosum*. Particularly preferred are *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncacea, Brassica oleracea, Glycine max*, and/or *Gossypium* sp.

A plant of the species *Beta vulgaris* is in particular a plant of the sub-species *Beta vulgaris* subsp. *maritima* (Seemangold) or *Beta vulgaris* subsp. *vulgaris*. These include, for example, *Beta vulgaris* subsp. *vulgaris* var. *altissima* (sugar beet in the narrower sense), *Beta vulgaris* ssp. *vulgaris* var. *vulgaris* (Mangold), *Beta vulgaris* ssp. *vulgaris* var. *conditiva* (beetroot), *Beta vulgaris* ssp. *vulgaris* var. *crassa/alba* (fodder beet).

Subject-matter of the present invention are also the plants that are obtained or obtainable by the methods described above or parts or seeds of the plants. Accordingly, one embodiment of the invention is a transgenic plant obtained or obtainable by the above method of transforming a plant cell and regenerating a plant from said cell, as well as progeny, seeds or parts thereof, wherein the progeny, the seed or the part comprises the at least one nucleotide sequence of interest as transgene, either stably or transiently. Another embodiment of the invention is a genetically modified plant obtained or obtainable by the above method of modifying the genome of a plant cell and regenerating a plant from said cell as well as progeny, seeds or parts thereof, wherein the progeny, the seed or the part comprises the modification in the genome introduced by the inventive method.

Parts of a plant includes plant organs like leaves, plant stems, stems, roots, vegetative buds, meristems, embryos, anthers, ovulae or fruit, plant tissues like callus tissue, storage tissue, meristematic tissue, embryogenic tissue, leaf tissue, bud tissue, root tissue, plant tumour tissue or reproductive tissue, includes plant cells like isolated plant cells with a cell wall or aggregates thereof or protoplasts, for example, and can mean a fusion of several organs, for example a flower or a seed or a part of an organ, for example a cross segment from the stem.

Further subject-matter of the present invention is a plant cell or a seed derived from the above transgenic plant or genetically modified plant. A plant cell derived from the above transgenic plant comprises the at least one nucleotide sequence of interest as transgene while a plant cell derived from the above genetically modified plant comprises the modification in its genome.

The invention will be further described with reference to the following Figures and Examples described herein. However, it is to be understood that the invention is not limited to such Examples.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Cray, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications, and publications or public disclosures (including publications on internet) referred to or cited herein are incorporated by reference in their entirety.

FIGURES

FIG. 1 shows the results of a qualitative analysis of callus induction in media supplemented with 0.5, 1.0 or 5.0 µM TSA. Control induction in medium without TSA is also shown. Ten explants per condition were randomly photographed.

Figure 2:
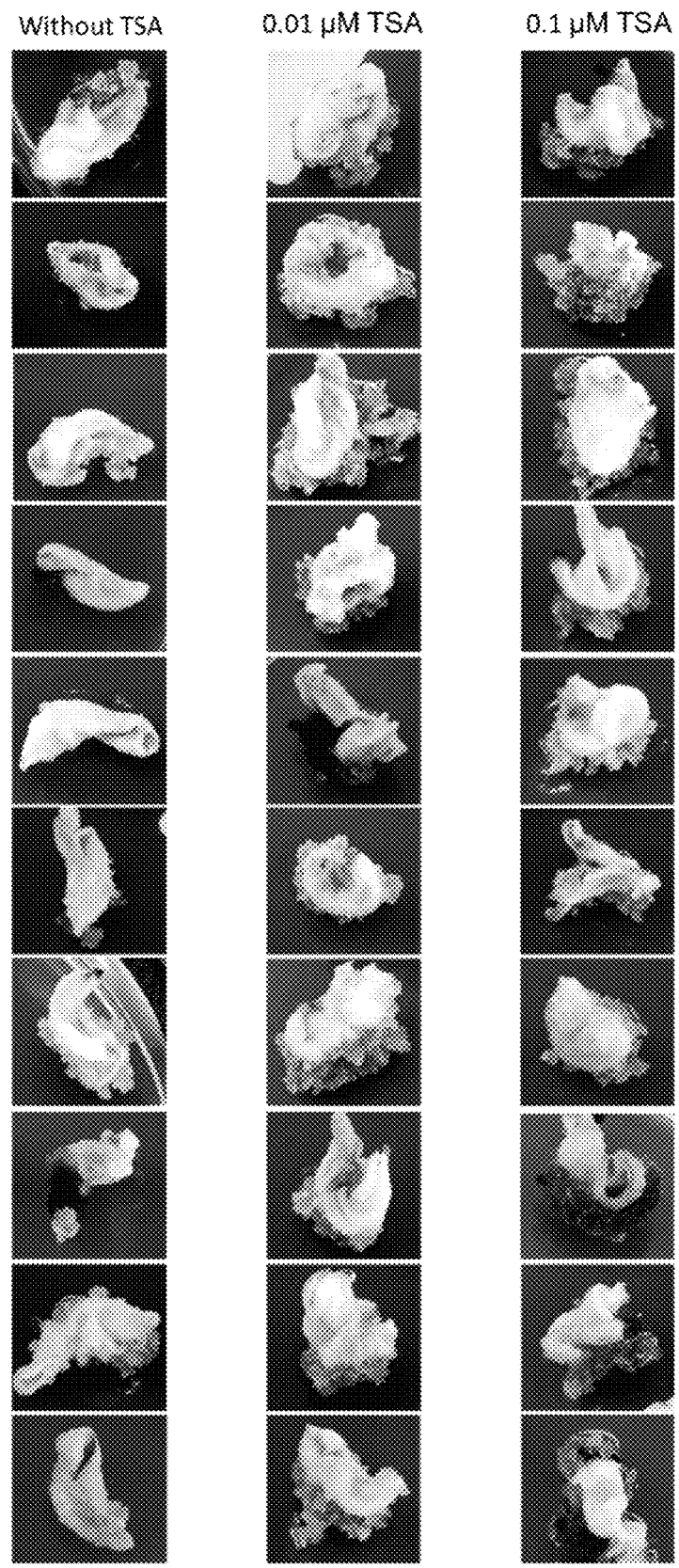

FIG. 2 shows the results of a qualitative analysis of callus induction in media supplemented with 0.01 or 0.1 µM TSA. Control induction in medium without TSA is also shown. Ten explants per condition were randomly photographed.

Figure 3:
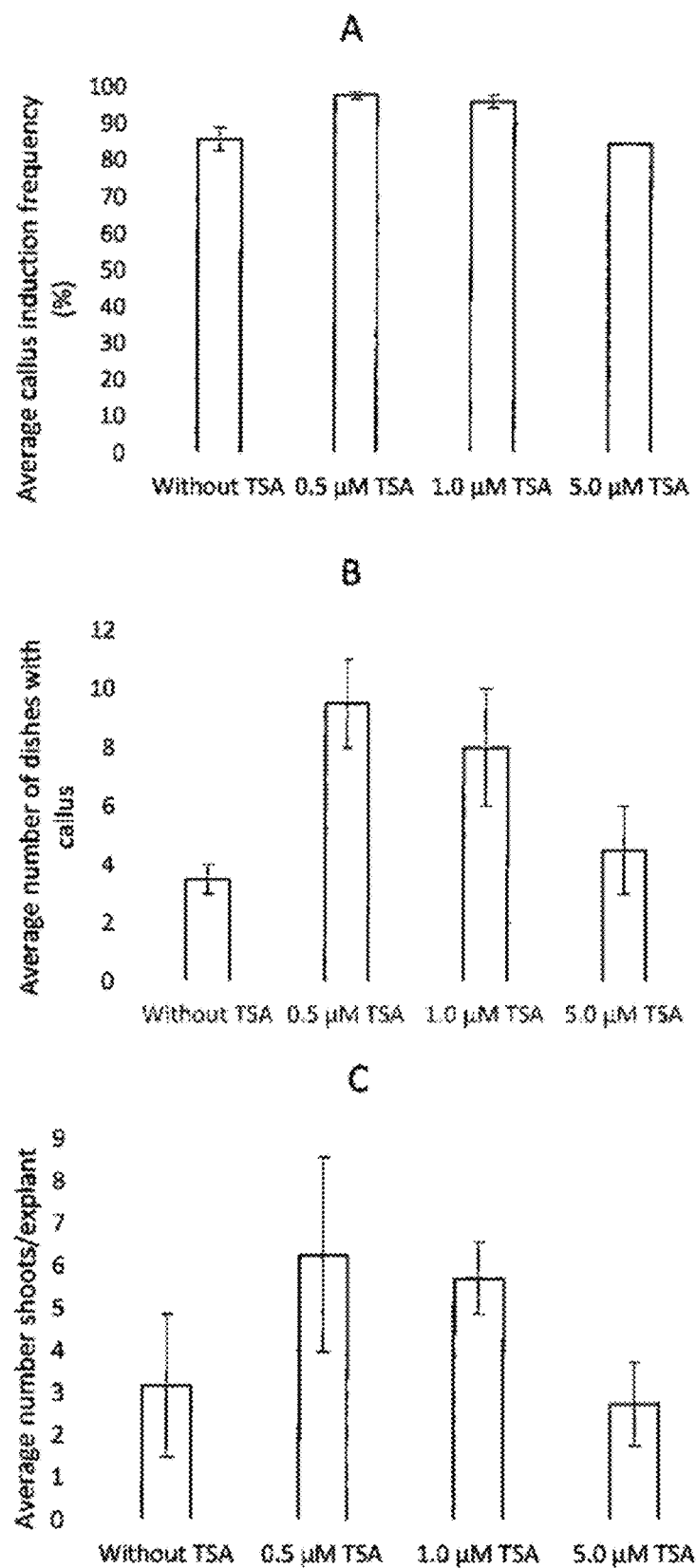

FIG. 3 shows bar diagrams demonstrating callus induction and plant regeneration using different amounts of TSA.

A: callus induction frequency of leaf explants incubated in medium supplemented with 0.5, 1.0 and 5.0 µM TSA.

B: amount of callus produced under each condition. The amount was estimated based on the number of dishes with harvested calli obtained in each variant.

C: shoot regeneration capacity based on the number of developed shoots per leaf explant used for each experimental condition.

Figure 4:
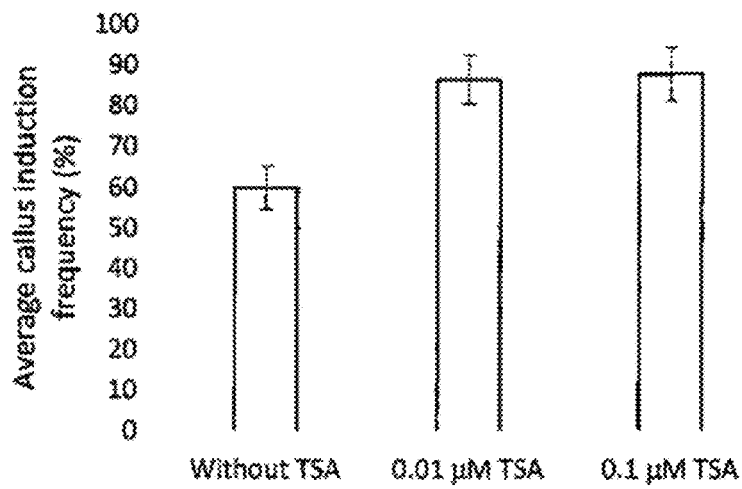
Figure 4:
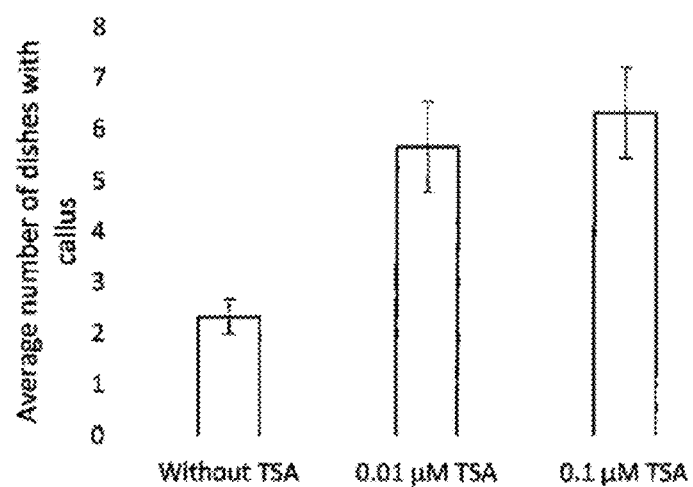
Figure 4:
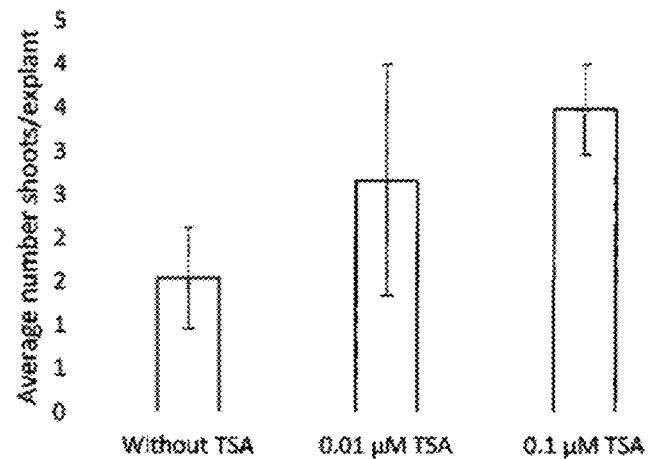

FIG. 4 shows bar diagrams demonstrating callus induction and plant regeneration using different amounts of TSA.

A: callus induction frequency of leaf explants incubated in medium supplemented with 0.01 and 0.1 µM TSA.

B: amount of callus produced in each condition. The amount was estimated based on the number of dishes with harvested calli obtained in each variant.

C: shoot regeneration capacity based on the number of developed shoots per leaf explant used for each experimental condition.

Figure 5:
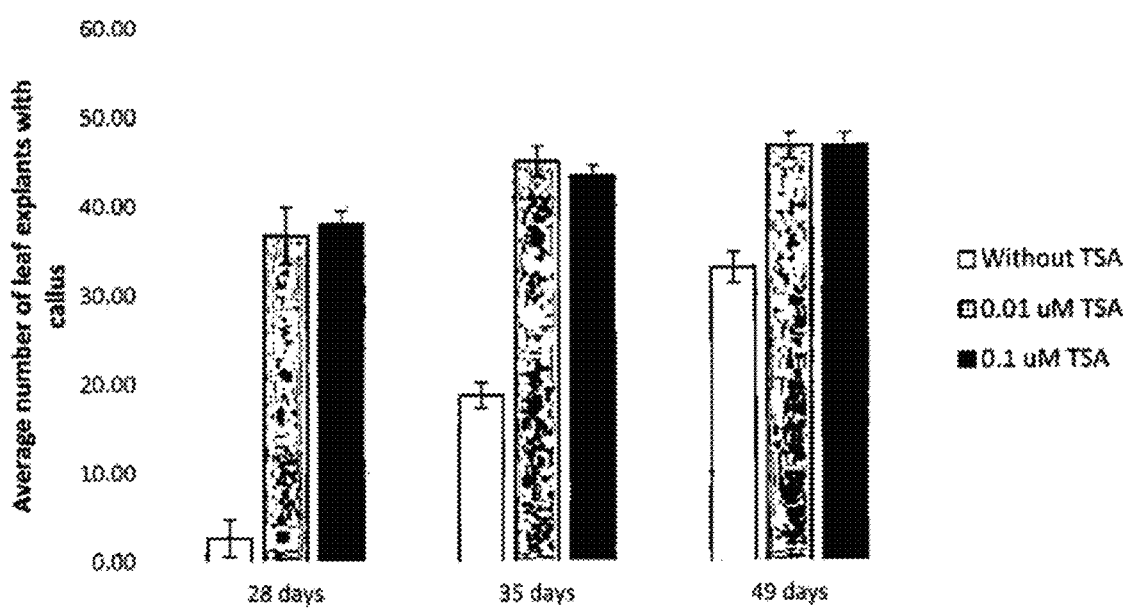

FIG. 5 is a diagram showing quantification of leaf explants with developing friable callus at 3 time points during callus induction. Medium was supplemented with different concentrations of TSA.

Figure 6:
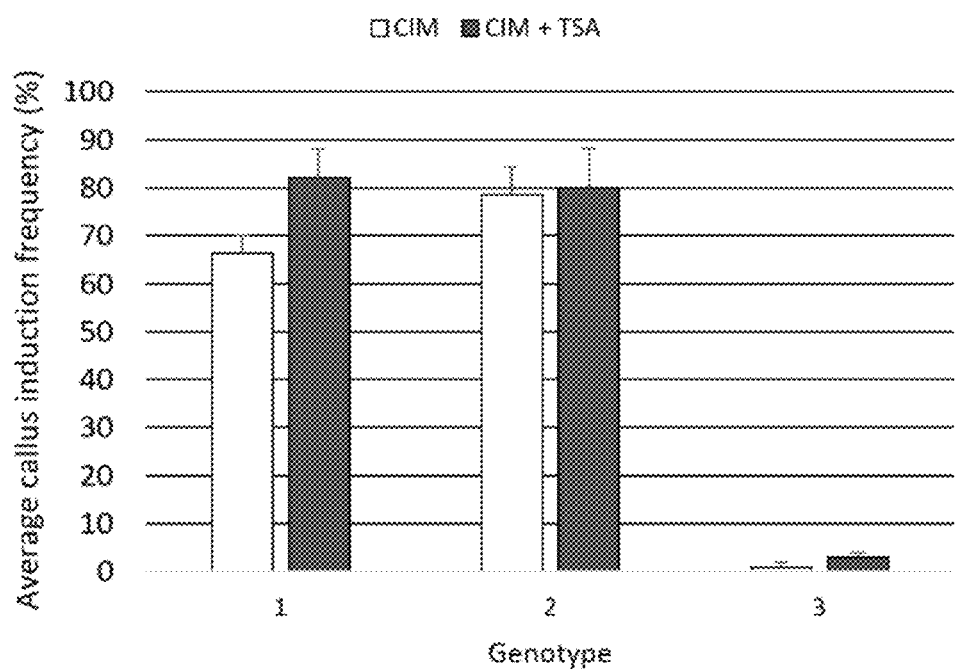
Figure 6:
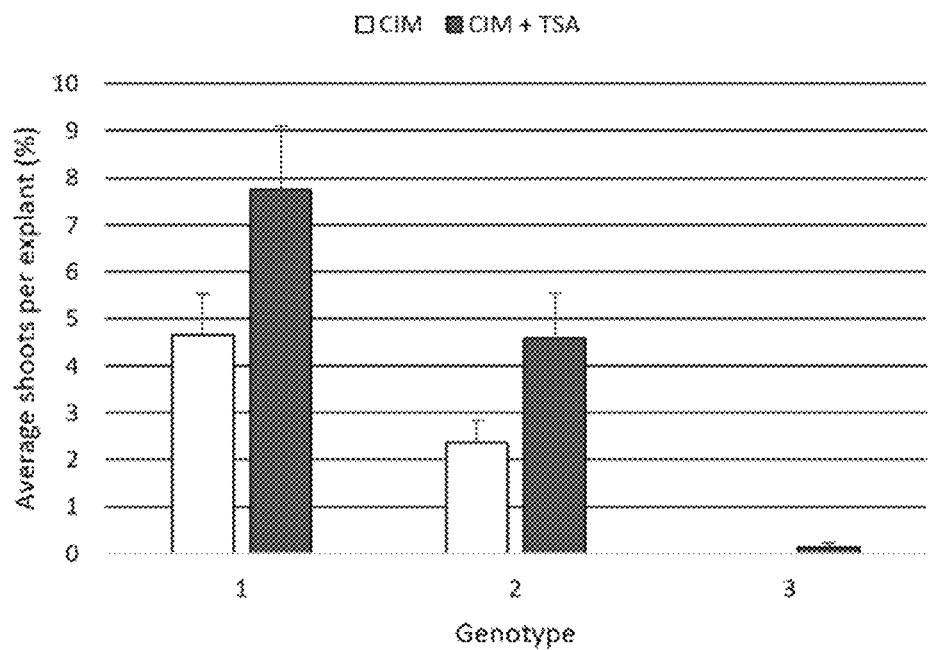

FIG. 6 Shoot regeneration of callus induced in medium supplemented with TSA is improved in recalcitrant genotypes. A: Average callus induction frequency of the control genotype (1), and two genotypes with either medium level (2) or high level (3) of shoot regeneration recalcitrance. Callus induction was performed in medium without TSA (white bar) or supplemented with 0.01 µM TSA (grey bar). B: shoot regeneration frequency of callus produced either in control medium (white bar) or in medium supplemented with 0.01 µM TSA (grey bar). Two experiments with 3 replicates per genotype were performed. Notice that the very recalcitrant genotype 3 is able to regenerate shoots only when the calli were produced in medium containing TSA.

EXAMPLES

1. Technical Description of the Sugar Beet Callus Induction Protocol

This method is based on the publication by Kischenko et al., 2005 Cell Biology International.

1. Micropropagated shoots of the genotype S706 were used as starting material. Shoots were multiplied in MS salts supplemented with 30 g/l sucrose and 0.25 mg/l benzyladenine (BAP).

2. To induce friable callus, leaf explants were isolated from micropropagated shoots and incubated in medium containing MS salts including 15 g/l sucrose and 2 mg/l BAP as a control and in the same medium supplemented with 0.01 µM TSA (B1), 0.1 µM TSA (B2), 0.5 µM TSA (B3), 1.0 µM TSA (B4), and 5.0 µM TSA (B5), at 28° C. in the dark for 7 weeks.

3. Development of callus from leaf explants was monitored during the incubation in the callus induction medium at 4, 5, 6 and 7 weeks.

4. Leaf explants producing friable calli were scored in order to calculate the callus induction frequency (percentage of leaf explants that produced friable calli).

An increased callus induction frequency has been observed when TSA is supplemented to the callus induction medium in a concentration range from 0.01 µM to 1.0 µM (FIG. 1, FIG. 2, FIG. 3A and FIG. 4A). The effect depends on the TSA concentration, since higher concentrations of TSA (e.g. 5.0 µM) seems to be cytotoxic. Furthermore, TSA increases the callus amount per leaf explant (FIGS. 3B and 4B).

2. Technical Description of the Shoot Regeneration Protocol

1. The friable calli of step 4 were harvested in medium containing MS salts, 30 g/l sucrose, 1 mg/l GA3 and 1 mg/l TDZ, and transferred to separate dishes.

2. The dishes were incubated under the light (16 h) at 24° C. for 10 days.

3. Developing shoots were counted under a stereomicroscope, in order to estimate the regeneration capacity (number of shoots per initial leaf explant).

3. Results

An increased number of regenerated shoots per explant has been observed (FIGS. 3C and 4C). Additionally, TSA accelerates the formation of callus and therefore shorten the time to produce transgenic events (FIG. 5). Already after 28 days a high number of leaf explants with developing calli occurred. Without application of TSA such number has not been reached even after 49 days. Further, first initial tests showed that by adding TSA, genotype-dependent recalcitrance to callus formation could be reduced.

Further experiments show that shoot regeneration of callus induced in medium (CIM) supplemented with TSA is improved in recalcitrant genotypes of Beta vulgaris. Genotypes 1 and 2 represent recalcitrant genotypes of Beta vulgaris from which only a small amount of plants can be regenerated from callus tissue by standard protocols. Genotype 3 is absolute recalcitrant, by known protocols a regeneration is not possible. Callus induction was performed in medium without TSA (white bar) or supplemented with 0.01 µM TSA (grey bar) (FIG. 6A). Shoot regeneration frequency of callus produced either in control medium (white bar) or in medium supplemented with 0.01 µM TSA (grey bar) (FIG. 6B). Two experiments with 3 replicates per genotype were performed. In genotype 1 the addition of TSA results in an increased formation of callus and an improved shoot regeneration capability of such callus: average callus induction frequency is increased from 66.3% to 82%, average number of shoots per explant from 4.7 to 7.7. For genotype 2 no significant increase of callus induction frequency has been observed, however the produced callus was obviously of improved quality, so that shoot regeneration capability was clearly enhanced: average number of shoots per explant is increased from 2.4 to 4.6. For the genotype 3 with the high level of recalcitrance the callus induction frequency is very low without and with TSA, perhaps slightly higher with TSA. Nevertheless, the regeneration of shoot from the produced calli were only possible if the callus has been induced in the presence of TSA.

The invention claimed is:

1. A method for inducing callus formation from at least one somatic or embryonic Beta vulgaris (B. vulgaris) plant cell, comprising the step of cultivating the at least one B. vulgaris plant cell in the presence of a histone deacetylase inhibitor (HDACi), wherein the step of cultivating the at least one B. vulgaris cell comprises:
   (i) introducing the HDACi into the at least one B. vulgaris plant cell;
   (ii) inducing callus formation from the at least one B. vulgaris plant cell of step (i) using callus-inducing medium; and
   (iii) obtaining a callus having enhanced capability of shoot regeneration,
   wherein the enhanced capability of shoot regeneration is determined by comparing to the same method for producing callus and the same genotype but without the use of the HDACi,
   wherein the embryonic B. vulgaris plant cell is a non-haploid cell, and
   wherein the HDACi is trichostatin A (TSA).

2. The method of claim 1, wherein the at least one B. vulgaris plant cell is a somatic or embryonic cell or is isolated from an explant or a part thereof isolated from a B. vulgaris plant.

3. The method of claim 1, wherein the step of cultivating the at least one B. vulgaris cell comprises:
   (i) growing the at least one B. vulgaris cell in a medium optionally comprising the HDACi, in a concentration of 0.01 to 5.0 µM, or (ii) introducing the HDACi into the at least one B. vulgaris cell, via bombardment, electroporation or microinjection.

4. A method for regenerating shoots from a callus tissue of B. vulgaris, comprising the following steps:
   (a) inducing callus formation from the at least one B. vulgaris plant cell according to the method of claim 1, and
   (b) cultivating the callus tissue obtained in step (a) under conditions promoting the growing of shoots out of the callus tissue.

5. A method for transforming a B. vulgaris plant cell, comprising the following steps:
   (a) producing callus having enhanced capability of shoot regeneration from the at least one B. vulgaris plant cell according to the method of claim 1, and
   (b) introducing into a B. vulgaris plant cell to be used in step (a) and/or into a cell of the callus obtained in step (a) at least one nucleotide sequence of interest.

6. A method for producing a transgenic B. vulgaris plant comprising the following steps:
   (a) transforming a B. vulgaris plant cell according to the method of claim 5, and
   (b) regenerating a transgenic B. vulgaris plant from the transgenic B. vulgaris cell resulting from step (a) or from a transgenic B. vulgaris cell derived therefrom.

7. A method for modifying the genome of a B. vulgaris plant cell, comprising the following steps:
   (a) inducing callus formation from the at least one B. vulgaris plant cell according to the method of claim 1, and
   (b) modifying the genome of a B. vulgaris plant cell to be used in step (a) and/or of a cell of the B. vulgaris tissue obtained in step (a) by introducing into said B. vulgaris cell a site specific effector enzyme which recognizes a predetermined site in the genome of said B. vulgaris cell, and optionally a repair nucleic acid molecule,
   wherein the modification of said genome is selected from:
   i. a replacement of at least one nucleotide; ii. a deletion of at least one nucleotide; iii. an insertion of at least one nucleotide; or iv. any combination of i.-iii.

8. A method of producing a B. vulgaris genetically modified plant, comprising the following steps:
   (a) modifying the genome of a B. vulgaris plant cell according to the method of claim 7, and
   (b) regenerating a B. vulgaris plant from the B. vulgaris cell resulting from step (a) or from a B. vulgaris cell derived therefrom.

9. The method of claim 3, wherein the medium is a callus induction medium.

10. The method of claim 9, wherein the at least one B. vulgaris cell is incubated in a solution comprising the HDACi before being transferred to the medium.

11. The method of claim 9, wherein the medium comprises the HDACi in a concentration of 0.01 to 5.0 μM.

\* \* \* \* \*